United States Patent [19]
Röckseisen

[11] Patent Number: 6,044,291
[45] Date of Patent: Mar. 28, 2000

[54] TARGETTING DEVICE FOR THE STRAIGHT-LINED INTRODUCTION OF AN INSTRUMENT INTO A HUMAN BODY

[75] Inventor: Armin Röckseisen, Scharnebeck, Germany

[73] Assignee: LAP GmbH, Luneburg, Germany

[21] Appl. No.: 09/067,362

[22] Filed: Apr. 27, 1998

[30] Foreign Application Priority Data

May 2, 1997 [DE] Germany ........................... 197 18 686

[51] Int. Cl.⁷ .................................................. A61B 5/05
[52] U.S. Cl. .......................................... 600/429; 378/206
[58] Field of Search ................................... 600/429, 417; 378/62–65, 68, 195, 204–206

[56] References Cited

U.S. PATENT DOCUMENTS

| | | | |
|---|---|---|---|
| 5,598,269 | 1/1997 | Kitaevich et al. | 356/399 |
| 5,675,625 | 10/1997 | Rockseisen | 378/206 |
| 5,707,360 | 1/1998 | Rockseisen | 604/116 |
| 5,782,842 | 7/1998 | Kloess et al. | 606/130 |

FOREIGN PATENT DOCUMENTS

| | | |
|---|---|---|
| 33092 | 12/1920 | Germany . |
| 92 18 321 U | 1/1994 | Germany . |
| 195 03 356 | 8/1996 | Germany . |

*Primary Examiner*—Brian L. Casler
*Attorney, Agent, or Firm*—Faegre & Benson LLP

[57] ABSTRACT

A targeting device for the straight-lined introduction of an instrument into a preferably human body with a movable light source for producing a projection in the targeting direction of the instrument. The piercing location and the directional angle of the piercing is evaluated with the help of a computer tomograph and the piercing location may be marked by a deposit, with a carriage which is traversable along a horizontal guide above the gantry of a computer tomograph and which can be fastened at any point on the horizontal guide. A laser light source is pivotably mounted about a horizontal axis, with an angular scale for indicating the horizontal pivoting angle of the laser light source, the vertical guide is arranged on the first carriage and the second carriage is traversable along the vertical guide and can be fastened at any point on the vertical guide. The laser light source is mounted on the second carriage and is also pivotable about a vertical axis and can be fastened at any pivoting angle. A second angular scale indicates the vertical pivoting angle.

24 Claims, 2 Drawing Sheets

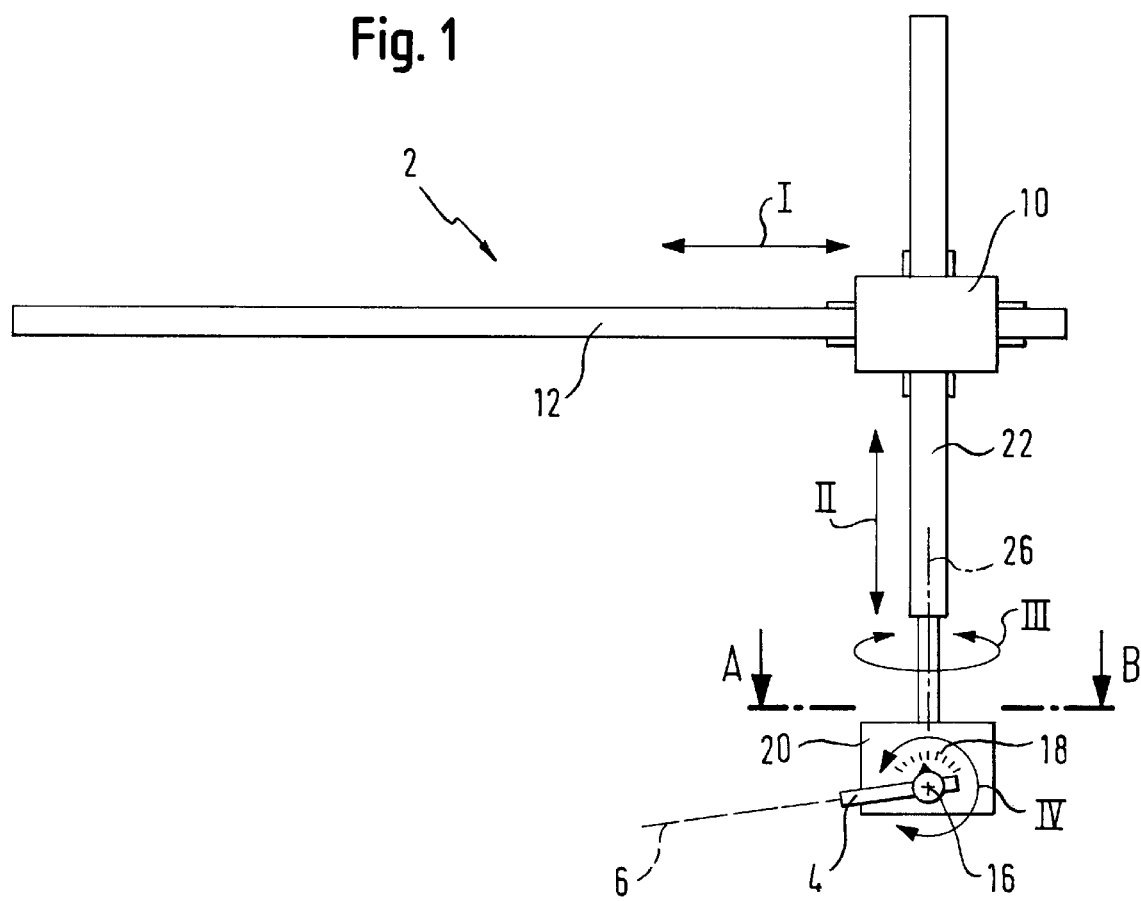
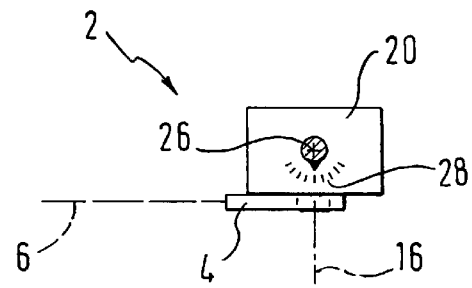

TARGETTING DEVICE FOR THE STRAIGHT-LINED INTRODUCTION OF AN INSTRUMENT INTO A HUMAN BODY

BACKGROUND OF THE INVENTION

The invention relates to a targetting device for the straight-lined introduction of an instrument into a preferably human body according to the introductory part of claim 1.

With a biopsy, needles are pierced into the body of a patient in order to remove tissue samples from a certain body location or to guide instruments to this location. It is known to locate and fix the target position with the help of a computer tomograph (CT). This produces virtual section images of the body in various sectional planes which usually lie over one another and are transversal. According to the CT-image the target location and the piercing location and thus the course of the piercing channel of the biopsy needle may be fixed. If the piercing cannot be effected perpendicularly from above or from the side because organs or bones lying in this access may not be touched, it is difficult to transfer the course of the piercing channel evaluated by way of the CT images in reality and to guide the long needle at the correct piercing angle. With a deviation from the determined piercing angle one however misses the target location and the procedure must be repeated, or even organs are damaged.

According to DE 92 18 321 there is known a positional indicator which produces at least one light beam directed onto the operation or treatment location on the patient body in order to indicate to the operator the location of operation and where appropriate the operational direction on the body of a patient. The position indicator for this is arranged on the front side of a computer tomograph housing via an arm which can be moved on all sides, with which four arm sections are linked onto one another by three joints. The arm is computer-controlled.

From DE 330 092 there is known a device for positional location of a point for operation technology purposes using a longitudinally displaceable rod as a probe which in a plane is so adjustable at any angle that the tip of the probe coincides with a predetermined point.

DE-OS 195 02 356 describes a targetting device for the straight-lined introduction of an instrument into a human body with a laser light source which is pivotably mounted about a horizontal axis on a carriage, wherein the carriage is adjustably guided and can be fixed along a horizontal guide above the gantry of a computer tomograph.

A computer-controlled device for actuating a position indicator is complicated in many respects. The degrees of freedom of the joints or the bearings of the device must be equipped with sensor technology and drives which permit a computer to recognize the present position and to move into a desired position. The control commands for moving the position indicator must be inputted via the computer in a long-winded manner and in the usual manner there is required a control of the drives in order to achieve positional accuracy.

A rod as an indicator or probe for direction evaluation of an instrument in an operation has the disadvantage that it cannot follow the distance to its holder which becomes larger on introduction of the instrument, it is annoying as a bulky object in an operating region which is any case is quite small, and because one is reliant on an unreliable directional judgement by the eye, only permits a limited accuracy of the directional orientation.

A laser light source as a targetting device, which can be horizontally displaced above the operated-on body and which can be pivoted about a horizontal axis is suitable, limited by the mentioned degrees of freedom, only for guiding an instrument along beams which can be adjusted in a plane fixed by the degrees of freedom.

SUMMARY OF THE INVENTION

It is therefore the object of the invention to provide a targetting device also without computer control for the straight-lined introduction of an instrument into a preferably human body, with which in a simple manner the instrument may be guided in the space at any previously appointed directional angle to the predetermined target location.

This object is achieved by the features of patent claim 1.

According to the invention a first carriage is adjustably guided above the gantry (introduction opening) of the computer tomograph along a horizontal guide, preferably along a transversal plane of the patient body and can be arrested at any point. On the first carriage there is arranged a vertical guide along which a second carriage is adjustable fastened and can be arrested at any point. The second carriage mounts a laser light source about a horizontal axis. Additionally the laser light source is mounted about a vertical axis. The laser light source projects a target marker, for example in the form of a point or a lined cross. On pivoting the laser light source the laser beam is correspondingly co-pivoted. On the carriage there are further attached two angular scales on which the pivoting angle of the laser device about the horizontal axis and about the vertical axis can be read off. In order to arrest the laser light source at a given location at a previously determined directional angle, the first and the second carriages can be fixed at any point of the respective guide and the laser light source can be fixed at any pivoting angle about the horizontal and vertical axis.

The horizontal guide is preferably a horizontally arranged rail which is fastened above the gantry on the housing of the computer tomograph. The first carriage is traversable and fastenable on the horizontally arranged rail. The vertical guide is preferably formed by a vertically arranged rail which is traversably and fastenably mounted on the first carriage. The vertical rail is either additionally pivotably mounted on the first carriage about the vertical axis—then the second carriage is preferably rigidly fastened on the vertical rail—or the second carriage is pivotably mounted on the vertical rail about the vertical axis.

The patient is traversed on a horizontally traversable rest into the gantry of a computer tomograph. The computer tomograph produces section images of the patient body usually in a vertical plane at right angles to the length of extension of the gantry, thus usually in the transversal plane of the patient. In this manner subsequent layer recordings of the patient body at certain distance from one another are made in the region in which the location to be treated in the patient and the expected piercing location on his skin is located. The relatively small distances of the layer recordings to one another permit a spacial perception of the arrangement of the organs in the inside of the patient in the region represented. In the layer recording in which the location to be treated is situated, firstly the directional angle about the horizontal axis for introducing the instrument may be determined. It is for example dependent on the shortest path to the body surface, on sensitive structures or organs in the environment of the location to be treated and on other damages in this region. If these influencing parameters do not permit access to the treatment location in the plane represented or for other reasons a diagonal access through neighbouring transversal planes with a directional angle component about the vertical axis is more suitable, then the neighbouring layer images are employed in order here, taking account of the imaged structures, to evaluate the piercing direction, i.e. the piercing angle (additionally about the vertical axis) as well as the piercing location. Known computer tomographs then permit the rest with the patient to again be traversed out of the gantry so far that the section plane with the previously determined piercing location comes to rest at a certain position outside of the gantry. The operator then marks the piercing location, for example with a pen compatable with the skin. As a result of this on the targetting device the directional angle about the horizontal axis and about the vertical axis which are evaluated as described above are adjusted. For the special case that alone the access is possible in the plane of the layer recording with the location to be treated, the targetting angle about the vertical axis is adjusted to zero so that the laser light source which is only pivoted about the horizontal axis only passes over the transversal plane of the layer recording concerned.

With a laser light source which is pivoted and arrested about the horizontal and vertical axis with respect to its directional angle the second carriage on which the laser light source is mounted is so traversed along the first and the second guide that the target marking projected by the laser light impinges on the patient body in the region of the piercing location marked by hand. The traversability of the laser light source along the horizontal and vertical guide is supplemented by the traversability of the rest into and out of the gantry in the sense that this gantry is aligned at right angles to the horizontal and vertical guide. In this manner the laser light source and the patient are traversable to one another in all three spacial directions and the target projection of the laser light source may, with an adjusted horizontal and vertical target direction angle, be guided onto the piercing location marked by hand. If then for example the tip of a biopsy needle is to be guided to the location to be treated in the patient body, then it is applied and so aligned on the piercing location which is marked by hand and at which also the target projection of the laser light source is located, that the target projection of the laser light source images on its rearward end, thus the end opposite to the tip. By way of this the biopsy needle is unambiguously aligned in the predetermined direction, and the direction remains recognizable also on introduction of the biopsy needle in that the target projection of the laser light source remains continually visible on the rearward end of the biopsy needle.

BRIEF DESCRIPTION OF THE DRAWINGS

A preferred embodiment form of the invention is hereinafter decribed by way of the attached drawings.

FIG. 1 shows a schematic front view of a targetting device according to the invention.

FIG. 2 shows a sectioned plan view of the targetting device taken along the line A–B in FIG. 1.

DETAILED DESCRIPTION OF THE INVENTION

Figure 3:
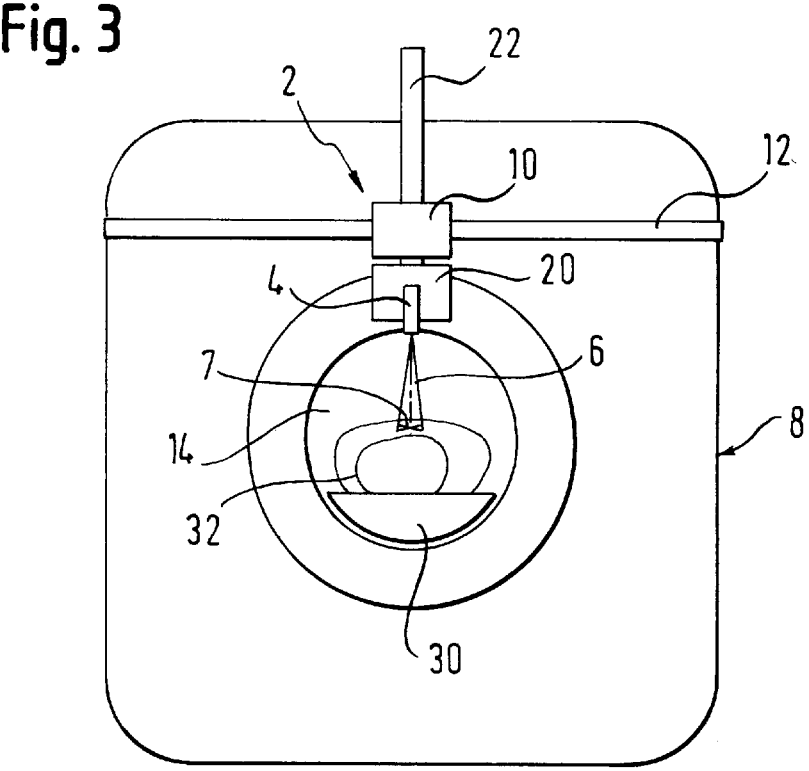
FIG. 3 shows a targetting device according to FIG. 1 on a computer tomograph above the gantry in a targetting angle position.

In FIGS. 1 and 2 there is shown a targetting device 2 with a laser light source 4 which projects a target marking in the form of a laser light beam 6 and which is pivotably mounted on a carriage 20 about the horizontal axis 16 along the arrow IV. The pivoting angle about the horizontal axis 16 can be read off from an angular scale 18. The carriage 20 is pivotably mounted on a vertical rail 22 about a vertical axis 26 along the arrow III. The pivoting angle about the vertical axis 26 can be read off from an angular scale 28. The vertical rail 22 is vertically traversably mounted on a carriage 10 in the direction of arrow II. The carriage 10 is horizontally traversably mounted on a horizontal rail 12 in the direction of arrow I.

Figure 4:
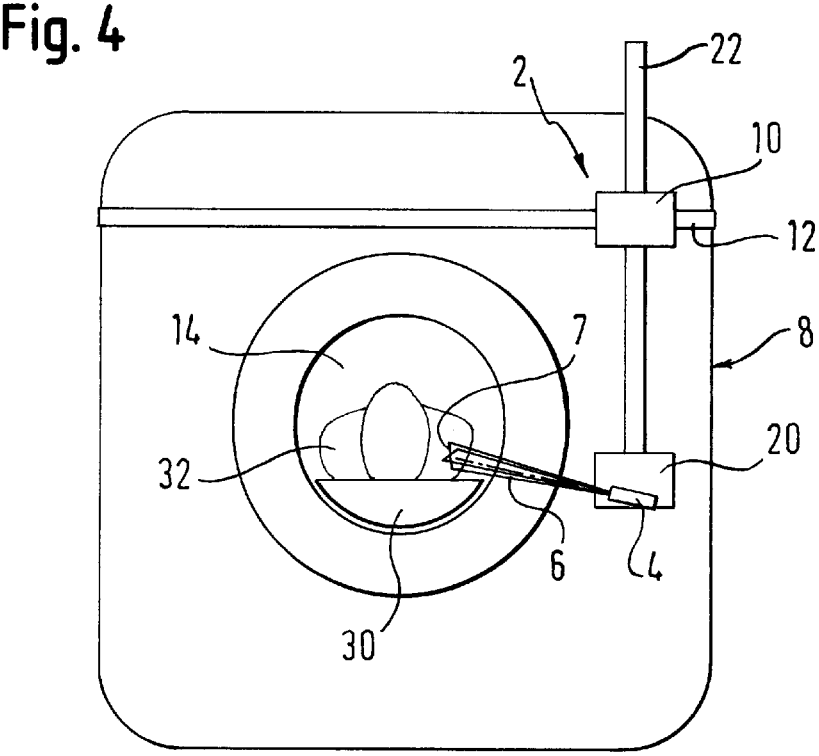
FIG. 4 shows the arrangement according to FIG. 3 in a second targetting angle position.

A targetting device of an instrument, for example a biopsy needle, which for example is to be determined by way of computer tomography pictures, is adjusted as a certain targetting angle position about the horizontal axis 16 and about the vertical axis 26 on the angular scales 18 and 28 and is fixed in this targetting direction. The laser light source 4 is then with the help of the targetting device 2 moved by traversing in the direction of arrows I and II such that the target projection 6 is projected on the piercing location of the body of a patient which has been previously marked by hand. This is shown in FIGS. 3 and 4. Here a lined cross 7 is projected onto two various positions of the body of the patient 32, which are envisaged as a piercing location, e.g. for a biopsy needle. In FIG. 3 it is indicated that the laser light source 4 projects the lined cross 7 frontally onto the rib-cage of the patient 32 who lies on a rest 30. In FIG. 4 the lined cross 7 is projected cranio-laterally onto the right shoulder. In both situations according to FIG. 3 and FIG. 4 the target directional angle is previously determined by way of CT images and the laser light source 4 is fixed in the correspondingly determined horizontal and vertical target directional angles and subsequently the horizontal rail 12 and the vertical rail 22 are traversed such that the lined cross is projected onto the piercing location previously marked by hand. The traversability of the rest 30 into the gantry and out of it at the same time represents the third translatory degree of freedom which is required in order to project the lined cross onto any position of the body surface of the patient 32.

I claim:

1. A targetting device for the straight-lined introduction of an instrument into a preferably human body comprising a movable laser light source for producing a projection in a targetting direction of the instrument, wherein a piercing location and a directional angle of a piercing is evaluated with the help of a computer tomograph and the piercing location may be marked by a deposit, including a first carriage which is traversable along a horizontal guide above a gantry of the computer tomograph and which is fastenable at any point on the horizontal guide, wherein the laser light source is pivotably linked, about a horizontal axis, to the first carriage with a first angular scale for indicating the horizontal pivoting angle of the laser light source, wherein a vertical guide is arranged on the first carriage, wherein a second carriage is traversable along the vertical guide and is fastenable at any point on the vertical guide, wherein the laser light source is mounted on the second carriage and is also pivotable about a vertical axis and is fastenable at any pivoting angle, and wherein a second angular scale is provided for indicating a vertical pivoting angle.

2. A device according to claim 1, wherein the laser light source projects a lined cross.

3. A device according to claim 2, wherein the horizontal guide is formed by a horizontally arranged rail which is fastened above the gantry on a housing of the computer tomograph, said first carriage being traversably and fastenably mounted on the horizontal rail.

4. A device according to claim 3, wherein the laser light source is pivotably mounted on the second carriage about the horizontal axis.

5. A device according to claim 4, wherein the vertical guide is formed by a vertically arranged rail which is vertically traversably mounted on the first carriage and is pivotably mounted about the vertical axis, said second carriage being fastened on the vertical rail.

6. A device according to claim 4, wherein the vertical guide is formed by a vertically arranged rail which is vertically traversably mounted on the first carriage, said second carriage being pivotably mounted on the vertical rail about the vertical axis.

7. A device according to claim 2, wherein the laser light source is pivotably mounted on the second carriage about the horizontal axis.

8. A device according to claim 7, wherein the vertical guide is formed by a vertically arranged rail which is vertically traversably mounted on the first carriage and is pivotably mounted about the vertical axis, said second carriage being fastened on the vertical rail.

9. A device according to claim 7, wherein the vertical guide is formed by a vertically arranged rail which is vertically traversably mounted on the first carriage, said second carriage being pivotably mounted on the vertical rail about the vertical axis.

10. A device according to claim 2, wherein the vertical guide is formed by a vertically arranged rail which is vertically traversably mounted on the first carriage and is pivotably mounted about the vertical axis, said second carriage being fastened on the vertical rail.

11. A device according to claim 3, wherein the vertical guide is formed by a vertically arranged rail which is vertically traversably mounted on the first carriage and is pivotably mounted about the vertical axis, said second carriage being fastened on the vertical rail.

12. A device according to claim 2, wherein the vertical guide is formed by a vertically arranged rail which is vertically traversably mounted on the first carriage, said second carriage being pivotably mounted on the vertical rail about the vertical axis.

13. A device according to claim 3, wherein the vertical guide is formed by a vertically arranged rail which is vertically traversably mounted on the first carriage, said second carriage being pivotably mounted on the vertical rail about the vertical axis.

14. A device according to claim 1, wherein the horizontal guide is formed by a horizontally arranged rail which is fastened above the gantry on a housing of the computer tomograph, said first carriage being traversably and fastenably mounted on the horizontal rail.

15. A device according to claim 14, wherein the laser light source is pivotably mounted on the second carriage about the horizontal axis.

16. A device according to claim 15, wherein the vertical guide is formed by a vertically arranged rail which is vertically traversably mounted on the first carriage and is pivotably mounted about the vertical axis, said second carriage being fastened on the vertical rail.

17. A device according to claim 15, wherein the vertical guide is formed by a vertically arranged rail which is vertically traversably mounted on the first carriage, said second carriage being pivotably mounted on the vertical rail about the vertical axis.

18. A device according to claim 14, wherein the vertical guide is formed by a vertically arranged rail which is vertically traversably mounted on the first carriage and is pivotably mounted about the vertical axis, said second carriage being fastened on the vertical rail.

19. A device according to claim 14, wherein the vertical guide is formed by a vertically arranged rail which is vertically traversably mounted on the first carriage, said second carriage being pivotably mounted on the vertical rail about the vertical axis.

20. A device according to claim 1, wherein the laser light source is pivotably mounted on the second carriage about the horizontal axis.

21. A device according to claim 20, wherein the vertical guide is formed by a vertically arranged rail which is vertically traversably mounted on the first carriage and is pivotably mounted about the vertical axis, said second carriage being fastened on the vertical rail.

22. A device according to claim 20, wherein the vertical guide is formed by a vertically arranged rail which is vertically traversably mounted on the first carriage, said second carriage being pivotably mounted on the vertical rail about the vertical axis.

23. A device according to claim 1, wherein the vertical guide is formed by a vertically arranged rail which is vertically traversably mounted on the first carriage and is pivotably mounted about the vertical axis, said second carriage being fastened on the vertical rail.

24. A device according to claim 1, wherein the vertical guide is formed by a vertically arranged rail which is vertically traversably mounted on the first carriage, said second carriage being pivotably mounted on the vertical rail about the vertical axis.

* * * * *